(12) United States Patent
Cho et al.

(10) Patent No.: US 12,234,266 B2
(45) Date of Patent: Feb. 25, 2025

(54) CRM197 PROTEIN EXPRESSION

(71) Applicant: OBI PHARMA, INC., Taipei (TW)

(72) Inventors: I-Ming Cho, Taipei (TW); Chia-Hung Chiu, Taipei (TW); Lee-Cheng Liu, Taipei (TW)

(73) Assignee: OBI PHARMA, INC., Taipei (TW)

( * ) Notice: Subject to any disclaimer, the term of this patent is extended or adjusted under 35 U.S.C. 154(b) by 1094 days.

(21) Appl. No.: 16/962,992

(22) PCT Filed: Jan. 18, 2019

(86) PCT No.: PCT/US2019/014156
§ 371 (c)(1),
(2) Date: Jul. 17, 2020

(87) PCT Pub. No.: WO2019/143911
PCT Pub. Date: Jul. 25, 2019

(65) Prior Publication Data
US 2023/0018689 A1    Jan. 19, 2023

Related U.S. Application Data

(60) Provisional application No. 62/619,449, filed on Jan. 19, 2018.

(51) Int. Cl.
*C07K 14/34*   (2006.01)
*C12N 15/70*   (2006.01)

(52) U.S. Cl.
CPC ............. *C07K 14/34* (2013.01); *C12N 15/70* (2013.01); *C07K 2319/02* (2013.01); *C07K 2319/034* (2013.01)

(58) Field of Classification Search
CPC ....................................................... C07K 14/34
USPC ............................................................ 435/488
See application file for complete search history.

(56) References Cited

U.S. PATENT DOCUMENTS 7,561,972 B1 * 7/2009 Welch .................... G16B 30/00
                                                              435/5
9,346,861 B2 * 5/2016 Dehottay ................ A61P 31/12

FOREIGN PATENT DOCUMENTS

WO     WO 2015/134402 A1 *  9/2015

OTHER PUBLICATIONS

Wang et al (Process Biochemistry, 2005, 40: 3068-3074).*
Bröker et al (Biologicals, 2011, 39: 195-204).*
Aminian et al (Protein Expression and Purification, 2007, 51: 170-178).*

* cited by examiner

*Primary Examiner* — Sean E Aeder
(74) *Attorney, Agent, or Firm* — Birch, Stewart, Kolasch & Birch, LLP

(57) ABSTRACT

The present invention relates to a method for producing CRM197 recombinant protein in cells. The method comprises culturing a cell comprising an expression plasmid with a polynucleotide and inducing expression of the CRM197 protein.

5 Claims, 12 Drawing Sheets
Specification includes a Sequence Listing.

(A)

(B)

(A)

(B)

CRM197 PROTEIN EXPRESSION

CROSS-REFERENCE TO RELATED APPLICATION

This application is a national phase entry under 35 U.S.C. § 371 of PCT Patent Application No. PCT/US2019/014156, filed on Jan. 18, 2019, which claims priority under 35 U.S.C. § 119 to U.S. Provisional Patent Application No. 62/619,449, filed Jan. 19, 2018, both of which are incorporated by reference. Also, the Sequence Listing filed electronically herewith is hereby incorporated by reference (File name: 2020-07-17T 253-002 Seq_List; File size: 6 KB; Date recorded: Jul. 17, 2020).

FIELD OF INVENTION

This present disclosure relates to the field of recombinant protein production in bacterial hosts. In particular, the present invention relates to a method for obtaining well-folded soluble recombinant CRM197 protein from bacterial cells. The present disclosure also relates to the expression plasmid and host cells of the recombinant CRM197 protein.

BACKGROUND OF THE INVENTION

Diphtheria toxin (DT) is a proteinaceous exotoxin that is synthesized by pathogen, e.g. *Corynebacterium diphtheria*. Toxigenic strains contain a bacteriophage lysogen carrying the toxic gene. DT is synthesized as a 535 amino acid polypeptides containing fragment A (catalytic domain) and fragment B (receptor binding and transmembrane domain) linked together by a disulfide bond. The toxin binds to a cell receptor (HB-EGF-receptor) and enters the cell by endocytosis where the fragment A released from the fragment B by proteolytic cleavage. Fragment A can inhibit protein translation by catalyzing the transfer of an ADP-ribosyl group to the N-1 of diphthamide at Histidine 715 in mammalian elongation factor 2 (EF-2). Hence, DT can kill eukaryotic cells by binding to cell surface receptors, entering the cytosol, and inactivating ribosomal EF-2.

The gene for cross-reacting material 197 (CRM197) is carried by the mutant phage β197$^{tox-}$. CRM197 is a nontoxic form of diphtheria toxin that contains a single amino acid substitution of glutamic acid to glycine (G52E) and loses its ADP-ribosyltransferase activity but retains binding activity. CRM197 is commonly used as carrier in polysaccharide or oligosaccharide conjugate vaccines. It is an ideal carrier for conjugate vaccine against encapsulated bacteria. Conjugate vaccines, comprising CRM197 covalently conjugated to poorly immunogenic and T-cell independent capsular polysaccharides, create conjugate antigens that are highly immunogenic and result in long-lasting immunity against the antigens. It has been widely used as carrier protein in several vaccines, e.g. Hib vaccine (Novartis Vaccines), heptavalent and 13-valent pneumococcal vaccine (Wyeth) and meningococcal serogroup C conjugate vaccine (Novartis Vaccines and Wyeth). Recent studies have suggested that CRM197 can inhibit heparin-binding epidermal growth factor (HB-EGF), an epidermal growth factor receptor (EGFR) ligand. EGFR and its ligand involve in cell development, proliferation and differentiation and can induce tumor formation.

In conclusion, CRM197 is a commonly used carrier protein in conjugated vaccines. Its high level of purity, homogeneous structure and availability of lysine residues allow the production of well-defined and characterized glycoconjugate vaccines. These attractive features of CRM197 have been used to develop a variety of CRM197-based conjugate vaccines with proven immunogenicity.

SUMMARY OF THE INVENTION

In the present application, a novel method is provided to produce a proper-folded soluble CRM197 protein, which is formed with correct disulfide linkage, e.g. two intra-disulfide bonds.

In one aspect, provided herein is a method of producing a CRM197 protein. The method comprises steps of culturing a bacterial cell comprising an expression plasmid having a polynucleotide; and inducing expression of the CRM197 protein. The polynucleotide comprises: (a) a CRM197 nucleotide sequence at least 90% identical to SEQ ID NO: 1, and (b) a secretion signal sequence encoding amino acids of SEQ ID NO: 2 at 5'-terminus of the CRM197 nucleotide sequence;

Preferably, the secretion signal sequence may be a pectate lyase B (PelB) sequence. More preferably, the PelB sequence may be from *Erwinia* spp.

Preferably, the expression plasmid may comprise a phosphate regulated promoter. More preferably, the phosphate regulated promoter may be a bacterial alkaline phosphatase A promoter.

Preferably, the bacterial cell may comprise *E. coli*. More preferably, the *E. coli* may be BL21 competent cell.

Preferably, the CRM197 protein may be soluble, periplasmic and/or properly folded. More preferably, the CRM197 protein may comprise intra-disulfide bonds.

Preferably, an expression temperature of the CRM197 protein is first incubating at 37° C. and then reducing to about 20-25° C.

Preferably, the induction is performed at pH 7.0-8.0 in a storage buffer.

Preferably, the storage buffer is selected from the group consisting of MOPS buffer, Tris buffer and Ammonium buffer In another aspect, provided herein is a polynucleotide. The polynucleotide comprises: (a) a CRM197 nucleotide sequence at least 90% identical to SEQ ID NO: 1, and (b) a secretion signal sequence encoding amino acids of SEQ ID NO: 2 located at 5'-terminus of the CRM197 nucleotide sequence.

In another aspect, provided herein is an expression plasmid. The expression plasmid comprises a polynucleotide mentioned above, and an inducible promoter to initiate expression of the polynucleotide.

In another aspect, provided herein is a host cell. The host cell comprises the polynucleotide mentioned above or the expression plasmid mentioned above.

In another aspect, provided herein is a CRM197 recombinant protein. The protein is produced by the expression plasmid deposited under ATCC Accession Number PTA-124609, deposited on Nov. 28, 2017.

In another aspect, provided herein is a CRM197 recombinant protein. The protein comprises (a) a polypeptide at least 90% identical to amino acids sequence transcribed from the nucleotides of SEQ ID NO: 1, and (b) a secretion signal sequence of SEQ ID NO: 2 at N-terminus of the polypeptide.

Other aspects of the invention will be apparent in view of the attached drawings and the following description.

DETAILED DESCRIPTION

Figure 1:
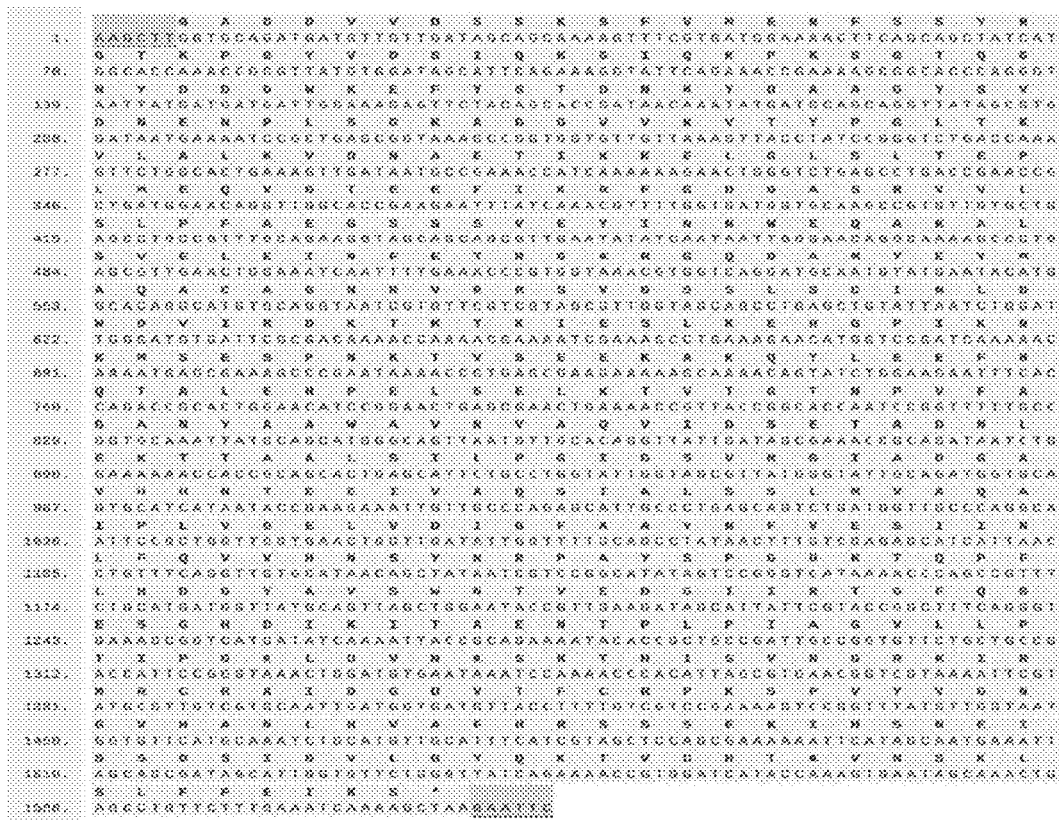
FIG. 1 illustrates sequence of CRM197 coding gene and amino acids. Sequence underlined are 5'-HindIII and 3' EcoRI restriction sites.

The foregoing and other aspects of the present disclosure will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process, or method.

The transitional phrase "consisting of" excludes any elements, steps, or ingredients not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

As used herein, the term "about" is used to indicate that a value includes for example, the inherent variation of error for a measuring device, the method being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the terms "transform," "transformed" or "introduce a nucleic acid into a host cell" refer to the application of any methods for introducing a foreign nucleic acid (such as a vector or plasmid) into a host cell with or without the presence of accompanying substances. The terms "transform a cell" or "transformed cell" suggest that a foreign nucleic acid is introduced into the cell or its daughter cells so that the host cell contains the foreign nucleic acid. Once introduced into the host cell, the nucleic acid is integrated with the chromosome and becomes a fragment thereof, or remains as an extrachromosomal element, for the purpose of replication. Transformation of an appropriate host cell with, for example, an expression vector can be achieved using known methods in the art, such as electroporation and particle bombardment, or using chemical methods such as catalyzing the transformation process with calcium phosphate. These methods are described in, for example, Maniatis et al., Molecular Cloning: A Laboratory Manual (Cold Spring Harbor Laboratory, 1982), or Ausubel et al., Current Protocols in Molecular Biology (John Wiley and Sons, 1994).

Unless otherwise defined, all technical and scientific terms used herein have the same meaning as commonly understood by one of ordinary skill in the art to which this invention belongs. All publications, patent applications, patents and other references cited herein are incorporated by reference in their entireties for the teachings relevant to the sentence and/or paragraph in which the reference is presented.

Embodiments according to an invention of the present application relate to methods for the production of a recombinant CRM197 protein.

A method in accordance with embodiments of the invention involves culturing a bacterial cell comprising an expression plasmid with a polynucleotide. After culturing, the cell, e.g. *E. coli*, is induced to express the CRM197 protein under optimal conditions so that over-expression of the recombinant CRM197 protein in soluble form was successfully achieved. Preferably, the cell is propagated or induced at a temperature from about 15° C. to about 37° C., more preferably 20-35° C., 20-30° C., or 20-25° C. This method will be helpful for the production and purification of the recombinant CRM197 at the native conformation and disulfide bonds.

The method may further comprise a step of cloning a codon optimized polynucleotide into an expression vector for transformation of bacterial cells such as, for example, an *E. coli* cell or a derivative or strain of *E. coli*. The polynucleotide comprises a CRM197 nucleotide sequence at least 90% identical to SEQ ID NO: 1, and a secretion signal sequence encoding amino acids of SEQ ID NO: 2 at 5'-terminus of the CRM197 nucleotide sequence. A pectate lyase B (PelB) sequence may be used as a leader sequence for the CRM197 protein so that the CRM197 protein expressed by the cell is soluble and is intracellular, periplasmic or secreted. In an embodiment, the PelB sequence may be from *Erwinia* spp. The secretion signal sequence may directly linked to the CRM197 nucleotide sequence. Alternatively, there may be a spacer between the secretion signal sequence and the CRM197 nucleotide sequence. The spacer may comprise more or less than 9 nucleotides such as, for example, between 5 and 20 nucleotides. In a preferred embodiment, the expression enhancer comprises a ribosome binding site upstream of the CRM197 nucleotide sequence and an ATG codon.

Embodies of the invention will be further illustrated with specific examples set forth below. One skilled in the art would appreciate that these examples are for illustration only an dare not intended to be limiting because variations and modifications are possible without departing from the scope of the invention.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

EXAMPLES

Example 1: Construction of pEGm-pho A 1.0 Vector, an Alkaline Phosphatase A Promoter-Derived Expression Vector Briefly, the codon optimized sequence of the target gene CRM197 was fused to various 5'-terminus signal sequences which can direct the expression of CRM197 to periplasm to achieve correct disulfide bond formation and proper protein folding. The recombinant CRM197 was operably linked to an expression control promoter under conditions suitable for expression. In a related aspect, the 5'-terminus signal sequence encodes a Sec-dependent signal sequence, such as PelB was fused to CRM197 for periplasmic expression. The optimized sequence of CRM197 gene (SEQ ID NO: 1) was synthesized in a pMK-RQ vector (CRM197_pMK-RQ) and several pairs of primers were used to insert signal sequence into 5'-terminus of CRM197 in pMK-RQ vector. The original CRM197 sequence was optimized and fused with various signal sequences, and was subsequently sub-cloned into an expression vector, e.g. pEGm-phoA 1.0, which contained a selection marker gene, such as kanamycin, and a phosphate-regulated promoter to control protein expression.

Specifically, pEGm-phoA 1.0 was modified from a commercially available vector pTAC-MAT-Tag®-2. Particularly. the selection marker, $Amp^R$, in the pTAC-MAT-Tag®-2 was replaced by $Kan^R$. In addition, the original pTAC promoter was also replaced by *E. coli* alkaline phosphatase A (phoA) promoter (Craig et. al., 1991). The pho A promoter in the expression vector of pEGm-phoA 1.0 was utilized to regulate the expression of CRM197 under a culture medium with fine control of phosphate concentration.

Example 1-1: Construction of Kanamycin Resistant Gene as Selection Marker

The DNA fragment of kanamycin resistant gene was amplified and obtained by a pairs of specific primers (Table 1, SEQ ID NO: 3 and SEQ ID NO: 4) using pET27b(+) plasmid as template. The vector backbone of pEGm-phoA 1.0 was also amplified by two specific primers (Table 1, SEQ ID NO: 5 and SEQ ID NO: 6) but without $Amp^R$ resistant gene using pTAC-MAT-Tag®-2 as template. Phusion high fidelity PCR kit was used in the amplification of these two DNA fragments and GeneArt® seamless cloning and assembly kit was further applied in cloning of the two DNA fragments to generate a modified pTAC-MAT-Tag®-2 vector with $Kan^R$ gene, named pTAC-MAT-Tag®-2-Kan.

TABLE 1

| SEQ ID NO: | Primer name | Sequence (5' → 3') |
|---|---|---|
| 3 | Kan-F | TGAAAAAGGAAGAGTATGAGCCATATTCAACGG |
| 4 | Kan-R | AACTTGGTCTGACAGTTAGAAAAACTCATCGAGCAT |
| 5 | pTAC-F | CTGTCAGACCAAGTTTACTCATATATAC |
| 6 | pTAC-R | ACTCTTCCTTTTTCAATATTATTGAA |
| 7 | phoA-pTAC-1-F | CTTTGTTTTTATTTTTTAATGTATTTGTACATAGGAGATATAATATGAAGCTTCCTCG |
| 8 | phoA-pTAC-1-R | CGACTATAAGTCTCGGCCGTGACAACTTTATGACAGAATTTCAGAAGGATCCTCTACGC |
| 9 | pelB-F | CTGCTCCTCGCTGCCCAGCCGGCGATGGCCGGTGCAGATGATGTTGTTGATA |
| 10 | pelB-R | CAGACCAGCAGCAGCGGTCGGCAGCAGGTATTTAAGCTTATGCGGCCTTGA |
| 11 | phoA-SEQ-F | GCGTAGAGGATCCTTCTGAAAT |
| 12 | pTAC-SEQ-R | CTGTATCAGGCTGAAAATCTTCTC |
| 13 | CRM197-433-F | GCAGCAGCGTTGAATATATCA |
| 14 | EG-197(II)-F | GCGAACTGAAAACCGTTACC |
| 15 | EG-197(II)-R | ACCAATACCAGGCAGAATGC |
| 16 | DXS-XhoI-F | ACTGCTCGAGTAAGTTTTGATATTGCCAAATACCCGACC |
| 17 | DXS-EcoRI-R | ACTGGAATTCTTATGCCAGCCAGGCCTTGA |

The sequence in grey area is a corresponding nucleotide sequence of pelB sequence.

Example 1-2: Replacement of pTAC Promoter by Pho A Promoter

The pTAC-MAT-Tag®-2-Kan was further used as template to amplify the whole vector with insertion of a pho A promoter sequence via two primers (Table 1, SEQ ID NO: 7 and SEQ ID NO: 8). The phoA promoter contains the Pho box sequence at the −35 (CTGTCATAAAGTTGTCAC) region (Craig et. al., 1991). Lastly, after DNA sequencing, we obtained two new constructs with the correct pho A promoter sequences. These new expression vectors were named pEGm-pho A 1.0 #2 and pEGm-pho A 1.0 #3.

Example 2: Construction of CRM197 Expression Plasmid

Example 2-1: CRM197 Gene Synthesis

Coding sequence of CRM197 gene was synthesized by GeneArt® (Life Technologies™) and codon usage was optimized for *E. coli* expression (FIG. 1). The synthesized CRM197 gene were inserted in pMK-RQ vector, named as CRM197_pMK-RQ, with two restriction sites for further cloning, 5'-HindIII and 3'-EcoRI.

Example 2-2: Insertion of pelB Signal Sequence at the 5'-Terminus of CRM197

To achieve proper folding and disulfide bond formation of CRM197 during protein synthesis, leader nucleotide sequence of pelB (pelBss) was inserted into the 5'-terminus of CRM197 coding sequence by amplified the CRM197pMK-RQ with two designed primers (Table 1, SEQ ID NO: 9 and SEQ ID NO: 10). pelB was a 22 amino acid peptide (MKYLLPTAAAGLLLLAAQPAMA; SEQ ID NO: 2) that can direct the fusion protein to the periplasmic space and will be removed by the endogenous signal peptidase. The new CRM197 construct was named pelBss-CRM197_pMK-RQ.

Example 2-3: Construction of pelBss-CRM197 to pEGm-phoA 1.0

Figure 2:
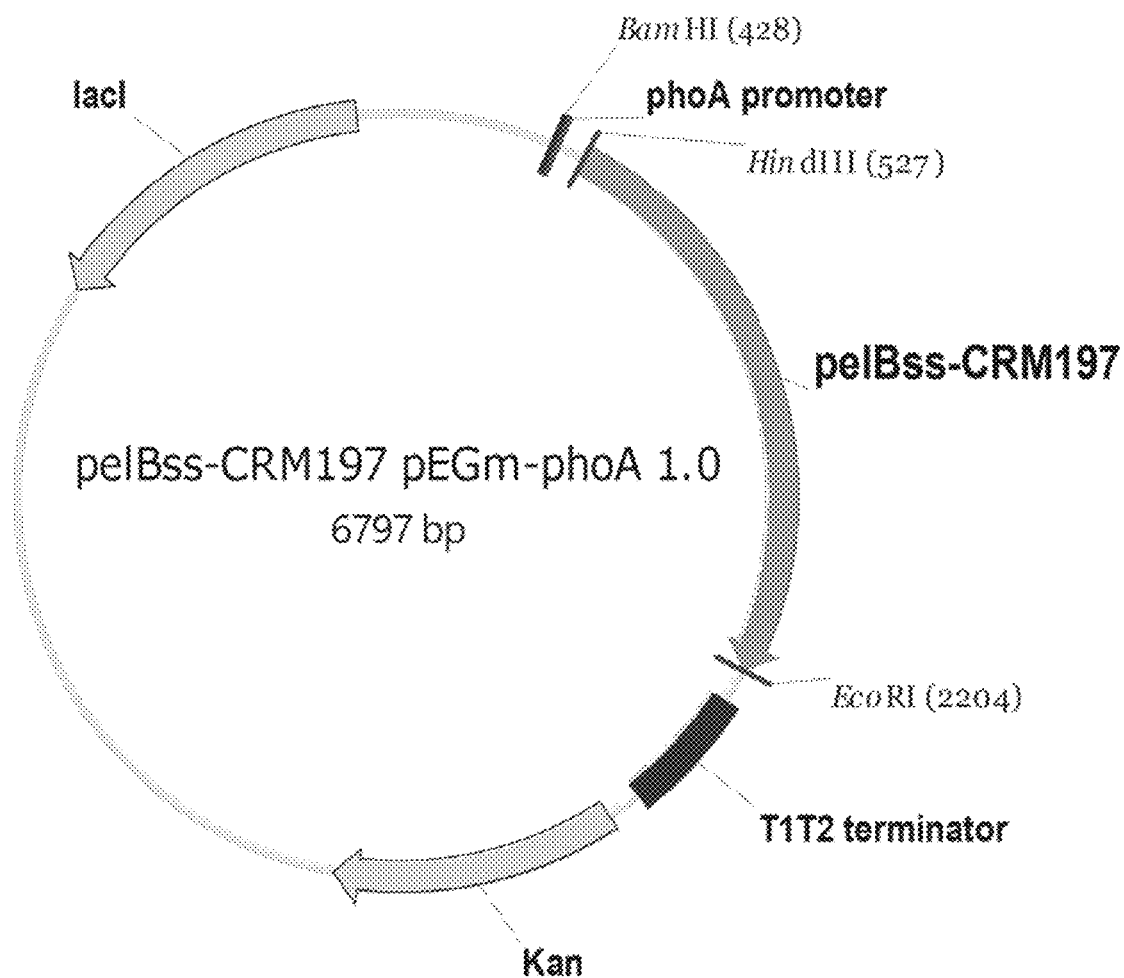
FIG. 2 illustrates plasmid map of pelBss-CRM197_pEGm-phoA 1.0.
Figure 3:
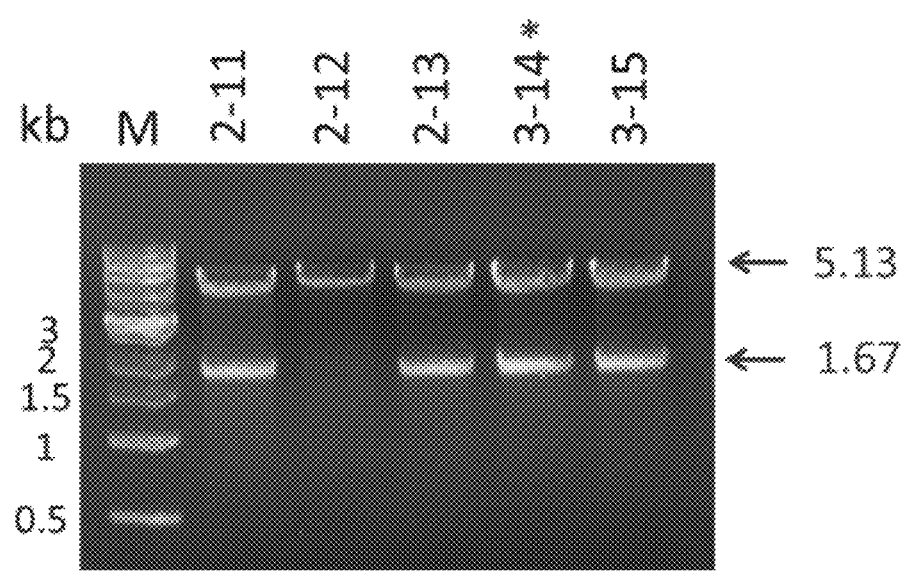
FIG. 3 illustrates agarose gel image of CRM197 construct. Five constructs were confirmed by HindIII and EcoRI restriction digestion and analyzed by 1% agarose gel. The correct construct should release~1.67 kb of CRM197 gene fragment. Construct #3-14 was further sent for DNA sequencing and confirmed with the correct CRM197 coding sequence.

The final step for the construction of CRM197 expression plasmid was to subclone pelBss-CRM197 gene to pEGm-phoA 1.0 vector by HindIII and EcoRI restriction sites to generate an expression plasmid, pelBss-CRM197_pEGm-phoA 1.0 (FIG. 2). We obtained several clones had the right size of CRM197 insert, about 1.67 kb. The construct #3-14 was confirmed having the correct pelBss-CRM197 coding sequence by sequencing and subsequently used for protein expression (FIG. 3).

Example 3: Expression Bacterial Strain Screening

Figure 4:
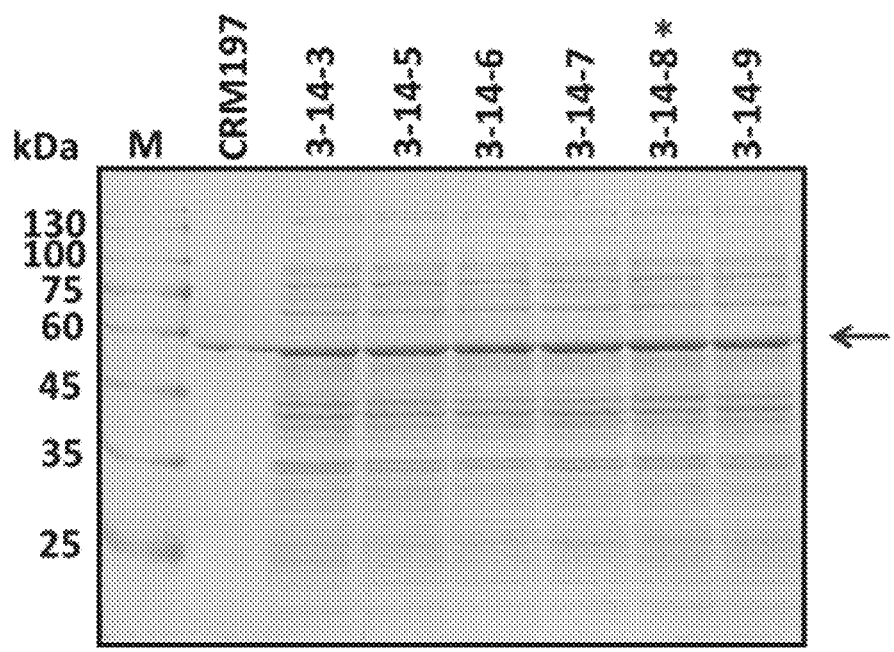
FIG. 4 illustrates SDS-PAGE analysis of CRM197 expression. (A) CRM197 construct #3-14 from FIG. 3 was transformed to competent cell BL21 and screened for CRM197 expression. Six transformants were examined under same expression condition. Same amount of total soluble form protein (6 μg) was analyzed by 10% SDS-PAGE. A strong induced protein band was observed at 58 kDa. All these transformants were shown comparable CRM197 expression. The strain 3-14-8 was chosen for further protein quality analysis. (B) Periplasmic expression of PelB-CRM197 at 28 and 45 hours of incubation. Arrow indicates CRM197 fusion protein.
Figure 4:
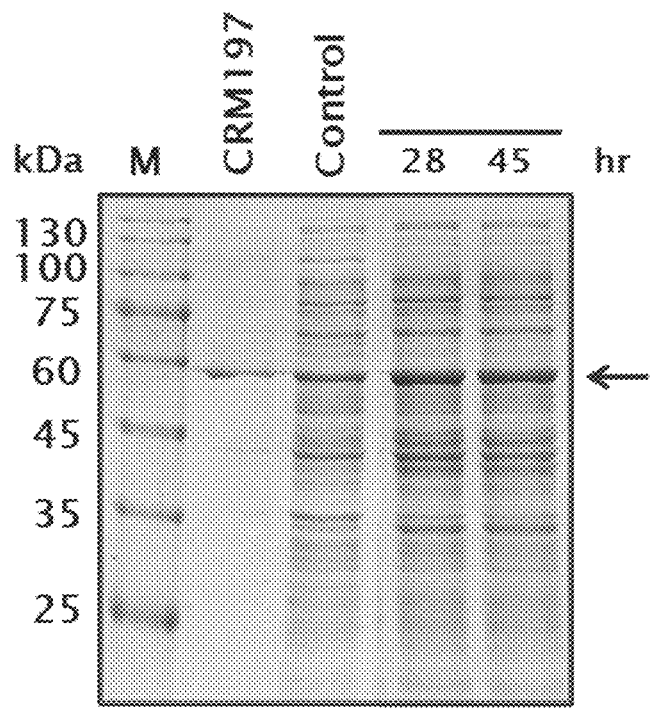

The expression vector pelBss-CRM197pEGm-phoA 1.0 #3-14 was transformed to *E. coli* BL21 strain and plated on LB agar plate (with 30 μg/ml kanamycin) at 37° C. overnight incubation to obtain several single-colony transformants. Six transformants were screened to select for the best CRM197 expression strain. The transformants were first inoculated in 5 ml LB broth (with 30 µg/ml kanamycin) in a 14 ml polypropylene tube at 37° C., 225 rpm for 5 hr, till $OD_{600}$ is about 1.0. Next, 0.5 mL culture of each strain was transferred into 50 mL of expression medium in a 250 ml flask at 37° C., 225 rpm for another 3 hr. The expression medium comprises 30 mM of ammonium sulfate; 2.4 mM of trisodium citrate dehydrate; 14.35 mM of potassium chloride; 1.07 g/L of yeast extract; 3.22 g/L of tryptone, 0.11 M of MOPS pH 8; 0.55% of glucose and 0.007 mM of magnesium sulphate. When $OD_{600}$ reaches to about 0.5-1, preferably 0.5, 0.6, 0.7, 0.8, 0.9 or 1.0, the temperature was shifted to about 16° C. to 25° C., preferably about 20° C. to 25° C., more preferably 20, 21, 22, 23 24 or 25° C., for 29 hr for CRM197 expression. The expression level of soluble CRM197 were further analyzed by SDS-PAGE to determine the candidate bacterial strain. Total 6 µg of each sample from supernatant fraction of the culture was loaded into a 10% SDS-PAGE for analysis (FIG. 4 (A)). The CRM197 expression level among these six strains looks comparable, strain #3-14-8 was chosen for further study.

In addition, FIG. 4(B) shows the expression of PelB-CRM197 at 28 and 45 hours of protein induction. The expression bacterial strains were cultured as the condition mentioned above but the induction times were 28 and 45 hr, respectively. From the result, the protein expression is similar at 28 and 45 hours of protein induction, indicating that the expression of PelB-CRM197 may be peaked at or before 28 hours of induction.

In addition, strain #3-14-8 was deposited under at The American Type Culture Collection (ATCC), 10801 University Boulevard, Manassas, VA 20110, USA, on Nov. 28, 2017, under ATCC Accession Number PTA-124609, and at Food Industry Research and Development Institute (FIRDI), 331 Shih-Pin Road, Hsinchu, Taiwan 300, R.O.C., on Dec. 7, 2017, under BCRC Accession Number BCRC 940662.

Example 3-A: Optimization of Induction Conditions

Example 3-A-1: Expression Medium

Periplasmic expression of PelB-CRM197 was tested in the medium with various buffer compositions, for example, 1M of MOPS, Tris or phosphate buffer. Strain #3-14-8 was inoculated and cultured in a medium with the addition of 1M of MOPS, Tris and phosphate buffer, pH 8. The cultured bacteria were harvested at different time points, i.e. 3 and 24 hours, to examine the effect of buffer composition on the expression level of CRM197. The cells harvested were disrupted by lysis buffer. 6 µg of soluble total protein were fractioned by 10% SDS-PAGE analysis.

Figure 5:
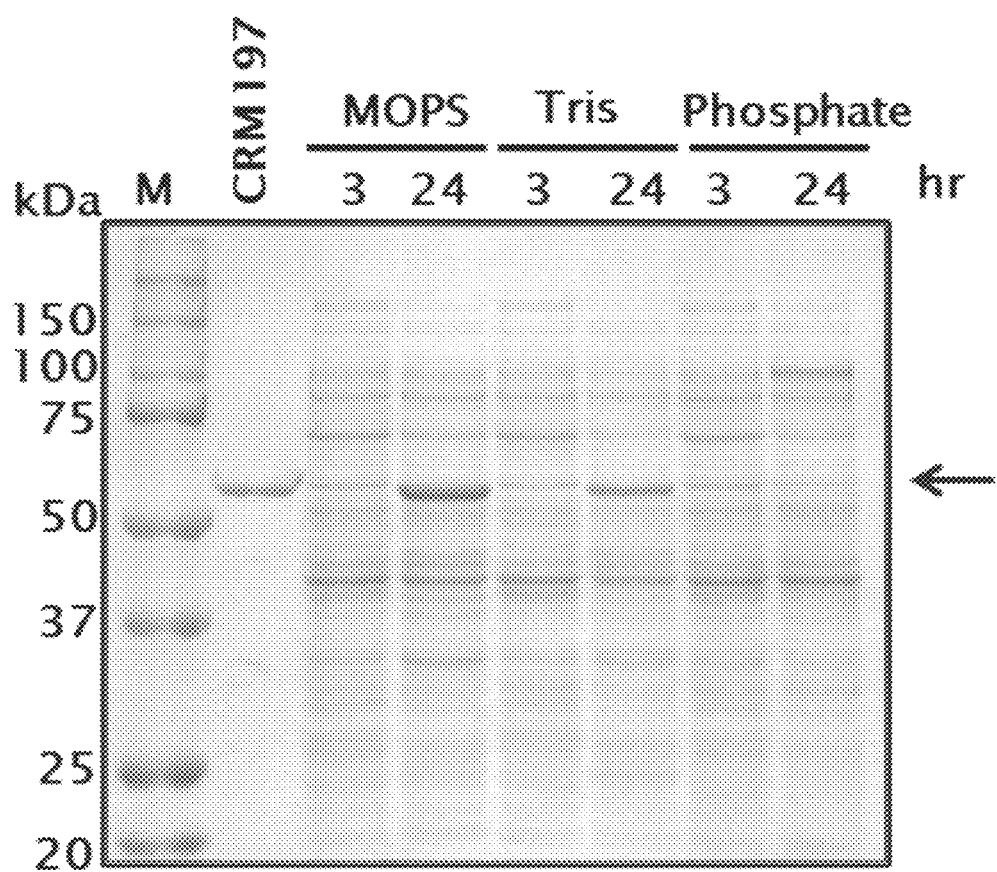
FIG. 5 illustrates expression of CRM197 fused with PelB signal sequence in *E. coli* BL21 strain in various medium.

The result in FIG. 5 shows that the medium in addition with MOPS induced most CRM197 protein expression after 24 hr of induction, followed by Tris and phosphate buffer.

Example 3-A-2: pH Value of the Expression Medium

Periplasmic expression of PelB-CRM197 was tested in the medium with various pH values of 1M MOPS, for example, pH 7.0, 7.5 or 8.0. Strain #3-14-8 was inoculated and cultured in a medium with various pH values of 7.0, 7.5 or 8.0. The cultured bacteria were harvested at different time points, i.e. 3 and 24 hours, to examine the effect of pH value on the expression level of CRM197. The cells harvested were disrupted by lysis buffer. 6 µg of soluble total protein were fractioned by 10% SDS-PAGE analysis.

Figure 6:
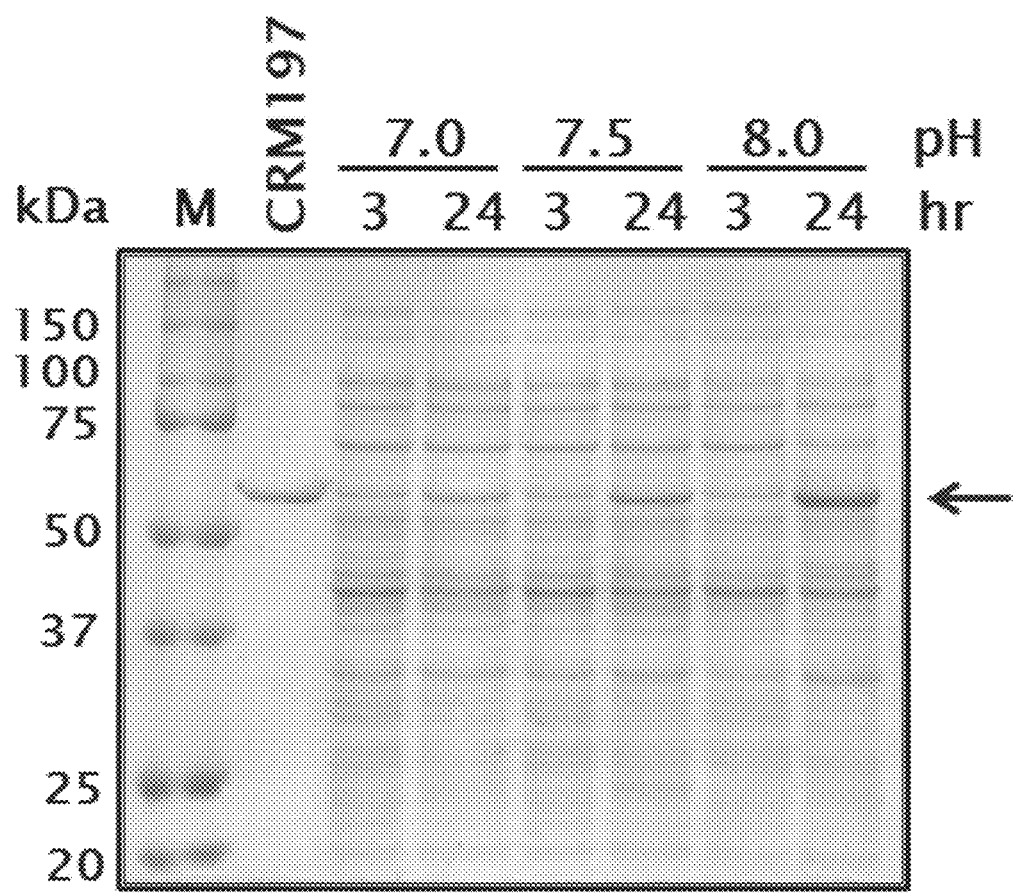
FIG. 6 illustrates expression of CRM197 fused with PelB signal sequence in *E. coli* BL21 strain in various pH values.

The result in FIG. 6 shows that the medium of pH 8.0 induced most CRM197 protein expression after 24 hr of induction, followed by 7.5 and 7.0.

Example 4: pelBss-CRM197 N-Terminus Cleavage Site Analysis

Figure 7A:
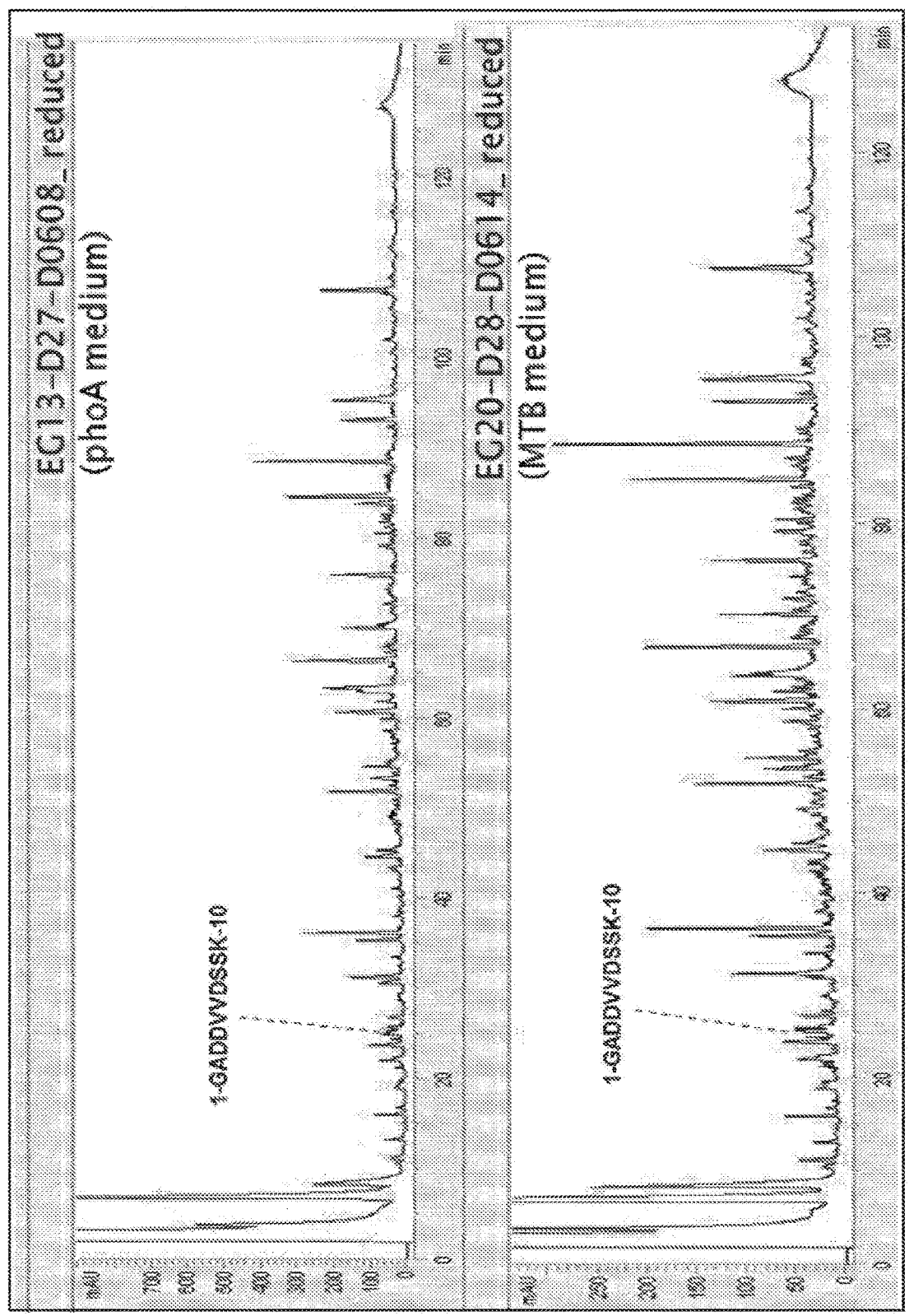
FIG. 7 illustrates results of recombinant pelBss-CRM197 cleavage site analysis. (A) RP-HPLC mapping of CRM197. One step DEAE-purified CRM197 from expression strain #3-14-8 was subjected to LC-MS analysis to confirm the cleavage site between pelB signal sequence and CRM197. The results above was shown that only the first 10-amino acid of CRM197 (1-GADDVVDSSK-10) was detected from both batches of samples (phoA and MTB as basal medium) suggesting that the pelB signal sequence was precisely and completely removed by the cellular protease. (B) CID spectrum of peptide at RT25.7. CID spectrum of peptide to confirm the peak in 7A (1-GADDVVDSSK-10) is indeed the first 10-amino acid of CRM197.
Figure 7B:
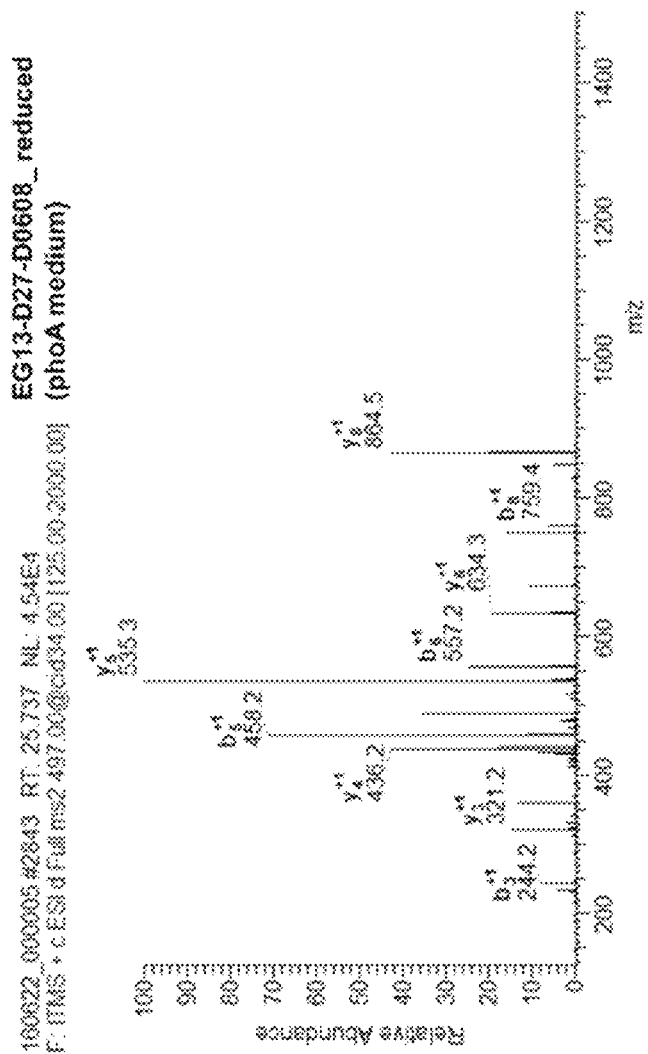

Since soluble form CRM197 was successfully expressed, it was then proceeding to examine whether pelB signal sequence had been precisely and completely removed from the CRM197 recombinant protein by the cellular protease. Therefore, partially purified CRM197 was subjected to liquid chromatography-mass spectrometry (LC-MS) analysis. For this experiment, two batches of CRM197 expression cells were prepared: one was cultured in phoA medium, the other was in fed-batch system using MTB as basal medium (yeast extract 24 g/L; phytone peptone 12 g/L; glycerol 8 g/L; sodium chloride 5 g/L; potassium phosphate monobasic 0.232 g/L; and potassium phosphate dibasic 1.643 g/L). The harvested cells were further subjected to one-step DEAE chromatography in order to obtain homogenized CRM197 for LC-MS analysis. The results of LC-MS and CID analysis (FIG. 7) were clearly shown no pelB signal sequence and no N-terminus truncated form of CRM197 protein were observed in these partially purified samples, suggesting the pelB signal sequence had been precisely and completely removed from the recombinant CRM197.

Example 5: pelBss-CR1VI197 Disulfide Bond Formation Analysis

Figure 8A:
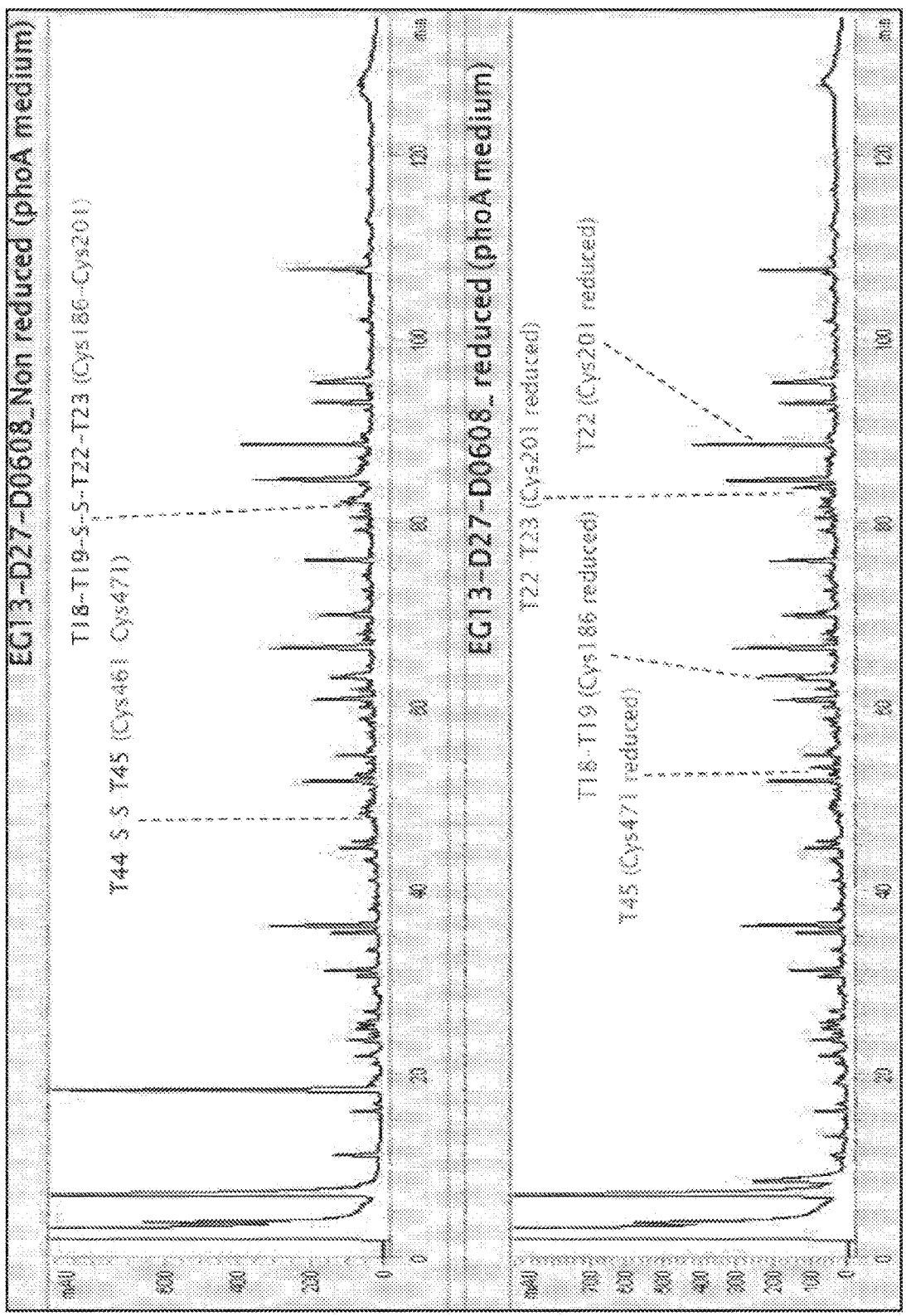
FIG. 8 illustrates results of CRM197 disulfide bond linkage analysis. (A) phoA medium based; (B) MTB medium based. One step DEAE-purified CRM197 from expression strain #3-14-8 was subjected to LC-MS analysis to examine whether CRM197 form correct disulfide linkages between Cys186-Cys201 and Cys461-Cys471. The results were revealed that two correct disulfide linkage were detected (T44-S-S-T45 and T18-T19-S-S-T22-T23) and no free sulfhydryl group and scrambling disulfide linkage were identified from both batches of samples.
Figure 8B:
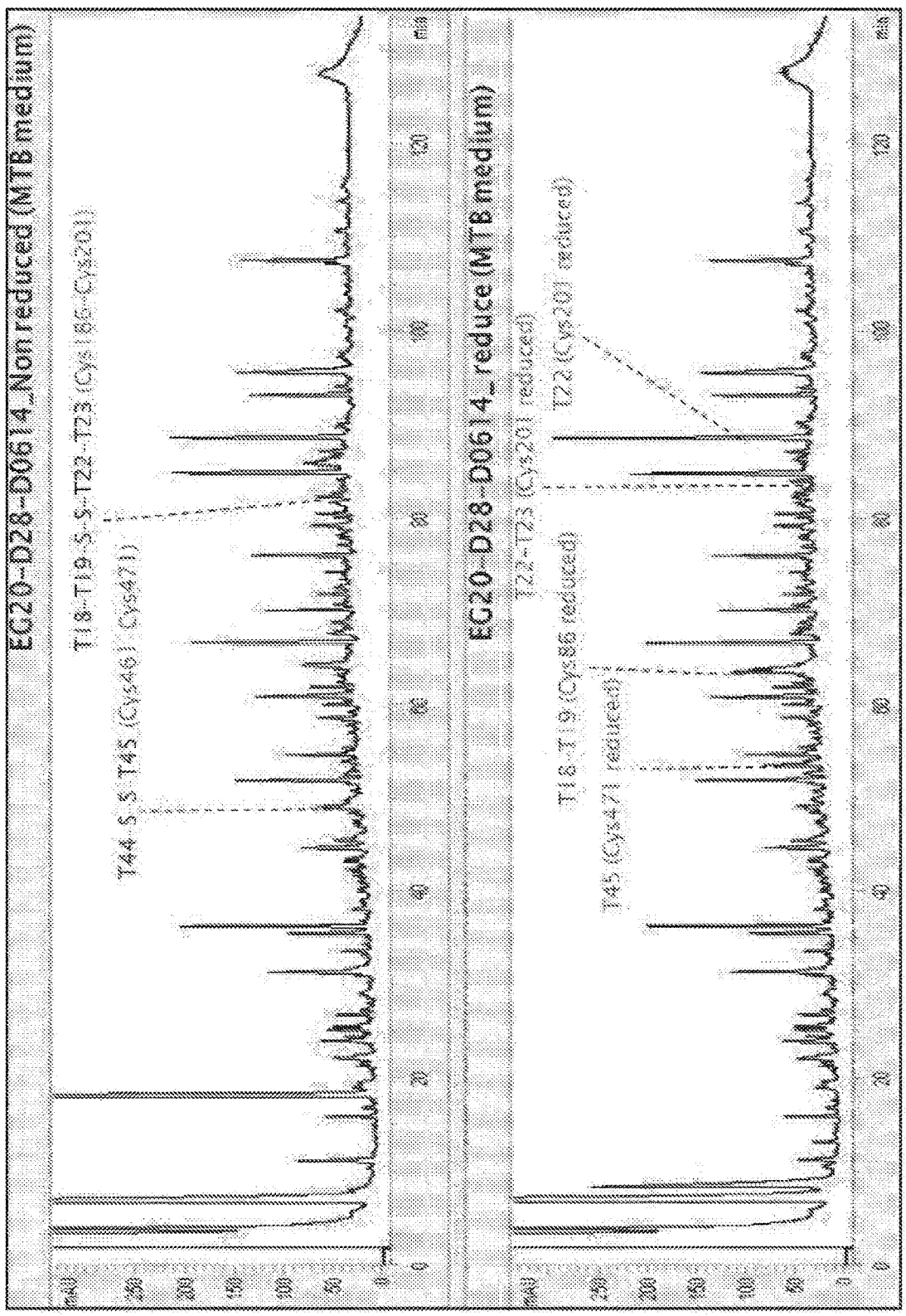

CRM197 contains four cystines and can form two intra-disulfide bonds between Cys186-Cys201 and Cys461-Cys471. Therefore, partially purified CRM197 above was also applied for disulfide linkage analysis. The results from FIG. 8 revealed that two disulfide linkages, Cys186-Cys201 and Cys461-Cys471, were identified in these two batches of CRM197 samples and no free sulfhydryl group and scrambling disulfide linkage were identified. The results indicate that the recombinant CRM197 product formed correct disulfide linkage.

Example 6: pelBss-CR1VI197_pEGm-phoA 1.0 BL21 #3-14-8 Bacterial Strain Stability Assay To comprehend the stability of CRM197 expression strain, e.g. strain #3-14-8, both protein expression and plasmid stability analysis were performed. To evaluate the strain stability after several generations of passage, bacterial strain was continuous cultured and maintained in exponential phase for up to 96 generations (doubling time is about 40 min in phoA medium, data not shown). In brief, one vial of pelBss-CRM197pEGm-phoA 1.0 BL21 #3-14-8 RCB were thawed and 0.4 mL of glycerol stock was inoculated in 40 ml of phoA medium (containing 30 µL/mL of kanamycin) in a 250 mL flask at 37° C., 225 rpm. When $OD_{600}$ reach to 1 (approximately 4 hr), 0.4 ml of culture broth was transferred to another flask with 40 ml of fresh phoA medium. This procedure was repeatedly performed for 16 times. Certain stages (6, 66 and 96 generations) of cultured cells were collected and the glycerol stocks were also generated and stored at −75° C. for further analysis.

Example 6-1: Protein Expression Stability Analysis

Figure 9:
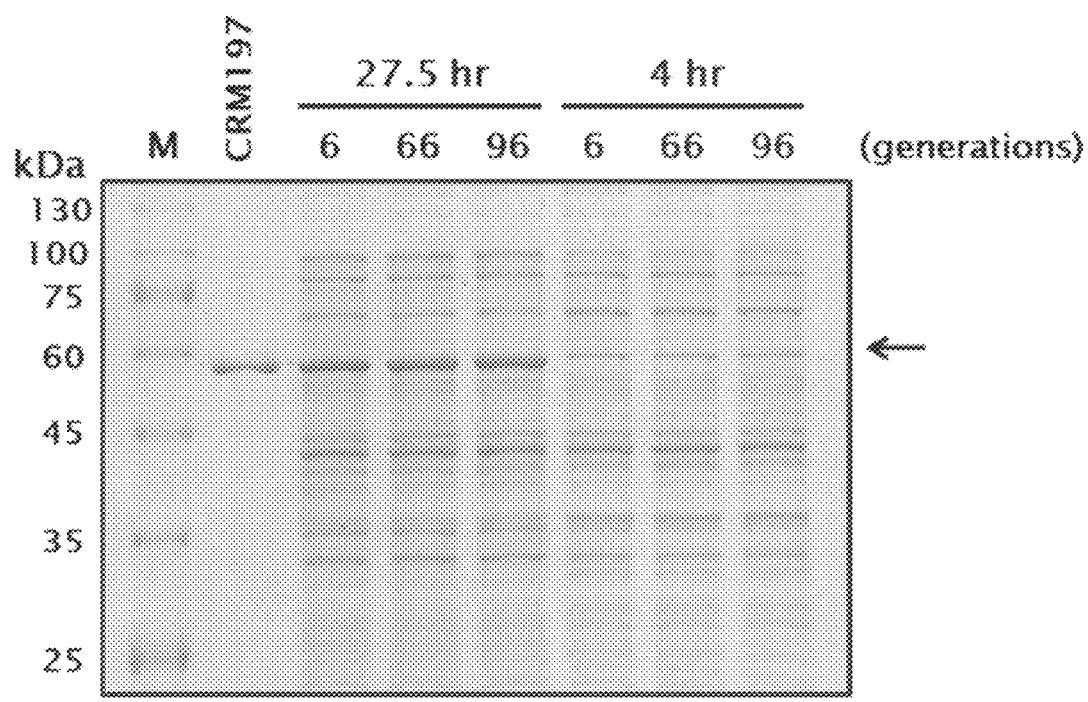
FIG. 9 illustrates results of CRM197 bacterial strain stability assay. (A) Results of protein expression stability analysis. CRM197 expression strain #3-14-8 collected from 6, 66 and 96-generations of passage were subjected to CRM197 expression under the same condition. Same amount of total soluble form protein (6 μg) was analyzed by 10% SDS-PAGE. Strong and comparable CRM197 expression level were observed in 6, 66 and 96-generations of passaged cells after 27.5 hr but not in 4 hr inoculation. (B, C) Results of plasmid restriction mapping analysis. Restriction enzyme digestion of pelBss-CRM197pEGm phoA 1.0 plasmid extracted from strain #3-14-8 after 6, 66 and 96-generations of passage. 0.5 μg of DNA was subjected for HindIII and EcoRI (B) or EcoRV (C) digestion at 37° C. for 1 hr and further analyzed by 1% agarose gel.
Figure 9:
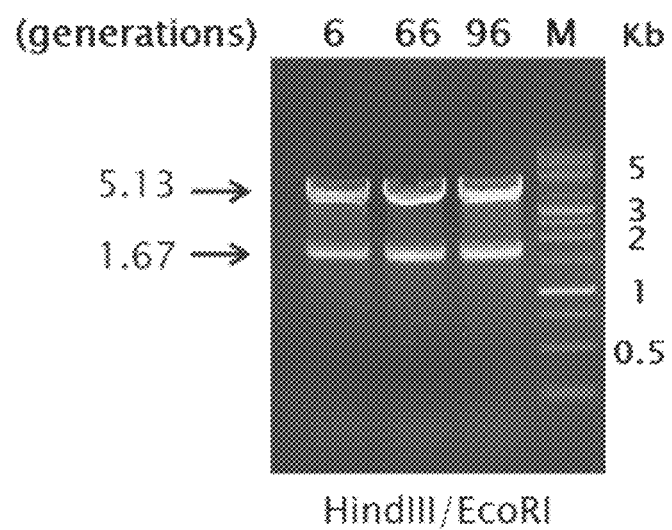
Figure 9:
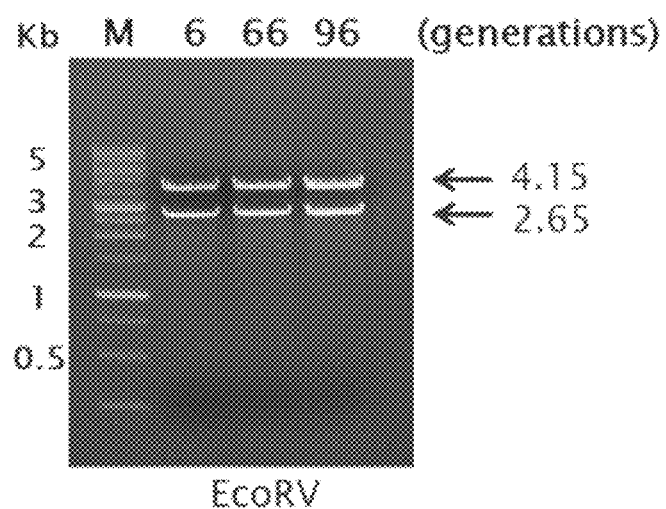

To examine the CRM197 expression stability, three different generations of CRM197 strain #3-14-8 were subjected for CRM197 expression. The protein expression procedure had been mentioned earlier and the final CRM197 expression analysis was shown in FIG. 9. The result was clearly shown that after 27.5 hr cultured in phoA medium, 6, 66 and 96-generations of cultured cells had comparable CRM197 expression level by 10% SDS-PAGE analysis (FIG. 9(A)). In addition, the $OD_{600}$ value measured after 4 and 27.5 hr incubation were very similar (Table 2): 0.552-0.592 at 4 hr and 3.402-3.576 at 27.5 hr, suggesting the similar growth rate of these three generations of strain. Consequently, pelBss-CRM197pEGm-phoA 1.0 BL21 #3-14-8 RCB maintained great expression stability up to 96 generations of passage.

TABLE 2

| Generations | $OD_{600}$ (4 hr) | $OD_{600}$ (27.5 hr) |
|---|---|---|
| 6 | 0.576 | 3.576 |
| 66 | 0.592 | 3.402 |
| 96 | 0.552 | 3.408 |

Example 6-2: Plasmid Stability Analysis

To confirm whether the CRM197 expression vector also retains its stability without deletion, duplication or inversion of DNA fragment, plasmids extracted from 6, 66 and 96 generations of cells were subjected to restriction enzyme digestion and DNA sequencing. Two sets of restriction enzymes were applied for plasmid digestion. HindIII and EcoRI can release the pelBss-CRM197 gene fragment (about 1.67 kb) and vector backbone (about 5.13 kb). On the other hand, EcoRV has two recognition sites in pelBss-CRM197pEGm-phoA 1.0, one at CRM197 gene and the other at kanamycin gene, which can release two DNA fragments (about 2.65 and 4.15 kb, respectively). The results of restriction mapping on FIGS. 9(B) and 9(C) revealed that the expected DNA fragments were observed when 0.5 μg of plasmid, from three different generations of cells, was digested by HindIII/EcoRI or EcoRV and analyzed by 1% agarose gel. In addition, the plasmid extracted from 96 generations of cells was also subjected to DNA sequencing (Table 1, SEQ ID NO: 11, SEQ ID NO: 12 and SEQ ID NO: 13) by Genomics BioSci & Tech and was confirmed the correct sequence of CRM197 coding gene (data not shown). Taken together, up to 96 generations of passage, the CRM197 expression strain of the present application still sustained steady plasmid stability.

Example 6-3: Plasmid Copy Number Retention Rate Analysis

Furthermore, the plasmid copy number retention rate after 96-generations of passage was examined. To do this, real-time quantitative-PCR (qPCR) based method was applied to determine plasmid copy number in *E. coli* (Lee et. al., 2006). In order to calculate absolute and relative plasmid copy number, two sets of primers were used to detect CRM197 gene in plasmid as target gene (Table 1, SEQ ID NO: 14 and SEQ ID NO: 15). DXS gene (D-1-deoxyxylulose 5-phosphate synthase) in host chromosome was used as reference gene (Table 1, SEQ ID NO: 16 and SEQ ID NO: 17). Since CRM197 and DXS are single-copy genes in vector and *E. coli* chromosome, the plasmid copy number can be determined as the ratio of CRM197/DXS. In order to calculate the exact copy number of plasmid (target gene) and reference gene, two standard linear lines were first generated to convert the plasmid molecules to Ct values by the known molecules (calculated from concentration) of pelBss-CRM197pEGm phoA 1.0 and DXSpEGm phoA 1.0. Next, the total DNA (containing pelBss-CRM197 plasmid and genomic DNA) extracted from 6, 66 and 96 generations of cells was subjected to qPCR and calculated the quantities of CRM197 gene (plasmid) and DXS gene (genome). Lastly, the absolute plasmid copy number were obtained by the number of CRM197DXS. The copy number retention rate was further calculated by dividing the plasmid copy number of 6-generation of sample as shown in Table 3. The results from two-time experiments revealed that the plasmid copy number retention rate still maintained at least 80% up to 96-generations of passage.

TABLE 3

| Generations | Detector Name | Ct | Copies | Copy number | Ratio |
|---|---|---|---|---|---|
| $1^{st}$ | | | | | |
| 6 | DXS | 17.8 | 3.80E+06 | — | — |
| 66 | DXS | 17.7 | 3.83E+06 | — | — |
| 96 | DXS | 18.7 | 2.19E+06 | — | — |
| 6 | CRM197 | 14.6 | 7.34E+06 | 19.3 | 1.0 |
| 66 | CRM197 | 13.3 | 1.68E+06 | 43.9 | 2.3 |
| 96 | CRM197 | 15.9 | 3.50E+06 | 16.0 | 0.8 |
| $2^{nd}$ | | | | | |
| 6 | DXS | 17.5 | 5.20E+06 | — | — |
| 66 | DXS | 17.7 | 4.54E+06 | — | — |
| 96 | DXS | 18.3 | 3.10E+06 | — | — |
| 6 | CRM197 | 14.4 | 9.65E+06 | 18.5 | 10 |
| 66 | CRM197 | 13.6 | 1.68E+06 | 37.0 | 2.0 |
| 96 | CRM197 | 15.7 | 4.39E+06 | 14.1 | 0.8 |

It will be apparent to those skilled in the art that various modifications and variations can be made to the disclosed embodiments. It is intended that the specification and examples be considered as exemplary only, with a true scope of the disclosure being indicated by the following claims and their equivalents.

REFERENCES

The references listed below and referred to herein are hereby incorporated into this specification by reference unless this specification expressly provides otherwise.

1. Craig, S. P. III, Yuan, L., Kuntz, D. A., McKerrow, J. H., and Wang, C. C., 1991. High level expression in *Escherichia coli* of soluble, enzymatically active schistosomal hypoxanthine/Guanine phosphoribosyltransferase and trypanosomal ornithine decarboxylase. *Proc. Natl. Acad. Sci. USA.* 88, 2500-2504.

2. Lee, C., Kim, J., Shin, S. G. and Hwang, S., 2006. Absolute and relative QPCR quantification of plasmid copy number in *Escherichia coli. J. Biotechnol.* 123, 273-280.

What is claimed is:

1. A method of producing a CRM197 protein, comprising culturing a cell comprising an expression plasmid having a polynucleotide, wherein the polynucleotide comprises:

(a) a CRM197 nucleotide sequence comprising SEQ ID NO: 1, and (b) a secretion signal sequence encoding amino acids of SEQ ID NO: 2 at 5'-terminus of the CRM197 nucleotide sequence; and inducing expression of the CRM197 protein, wherein the induction is performed at pH 7.5-8.0 in an expression medium, and an expression temperature of the CRM197 protein is first incubating at 37° C. and then reducing to about 20-25° C., wherein the expression plasmid comprises a phosphate regulated promoter, and the cell comprises *E. coli,* wherein the phosphate regulated promoter is a bacterial alkaline phosphatase A promoter; and the CRM197 protein is soluble, periplasmic, and folded and comprises two intra-disulfide bonds.

2. The method of claim 1, wherein the secretion signal sequence is from *Erwinia* spp.

3. A expression plasmid, comprising a polynucleotide of comprising:

(a) a CRM197 nucleotide sequence at least 90% identical to SEQ ID NO: 1, and (b) a secretion signal sequence encoding amino acids of SEQ ID NO: 2 at 5'-terminus of the CRM197 nucleotide sequence; and an inducible promoter to initiate an expression of the polynucleotide, wherein the inducible promoter comprises a phosphate regulated promoter, wherein the expression plasmid is deposited under ATCC Accession Number PTA-124609 on Nov. 28, 2017.

4. A host cell comprising the expression plasmid of claim 3.

5. The method of claim 1, wherein the induction is performed in the expression medium with a MOPS buffer.

* * * * *

SEQUENCE LISTING

<160> NUMBER OF SEQ ID NOS: 17

<210> SEQ ID NO 1
<211> LENGTH: 1608
<212> TYPE: DNA
<213> ORGANISM: Artificial Sequence
<220> FEATURE:
<223> OTHER INFORMATION: CRM197 DNA sequence

<400> SEQUENCE: 1

| | | | | |
|---|---|---|---|---|
| ggtgcagatg atgttgttga tagcagcaaa agtttcgtga tggaaaactt cagcagctat | 60 |
| catggcacca aaccgggtta tgtggatagc attcagaaag gtattcagaa accgaaaagc | 120 |
| ggcacccagg gtaattatga tgatgattgg aaagagttct acagcaccga taacaaatat | 180 |
| gatgcagcag gttatagcgt ggataatgaa atccgctga cggtaaagc cggtggtgtt | 240 |
| gttaaagtta cctatccggg tctgaccaaa gttctggcac tgaaagttga taatgccgaa | 300 |
| accatcaaaa aagaactggg tctgagcctg accgaaccgc tgatggaaca ggttggcacc | 360 |
| gaagaattta tcaaacgttt tggtgatggt gcaagccgtg ttgtgctgag cctgccgttt | 420 |
| gcagaaggta gcagcagcgt tgaatatatc aataattggg aacaggcaaa agccctgagc | 480 |
| gttgaactgg aaatcaattt tgaaacccgt ggtaaacgtg gtcaggatgc aatgtatgaa | 540 |
| tacatggcac aggcatgtgc aggtaatcgt gttcgtcgta cgttggtag cagcctgagc | 600 |
| tgtattaatc tggattggga tgtgattcgc gacaaaacca aaacgaaaat cgaaagcctg | 660 |
| aaagaacatg gtccgatcaa aaacaaaatg agcgaaagcc cgaataaaac cgtgagcgaa | 720 |
| gaaaaagcaa acagtatct ggaagaattt caccagaccg cactggaaca tccggaactg | 780 |
| agcgaactga aaaccgttac cggcaccaat ccggtttttg ccggtgcaaa ttatgcagca | 840 |
| tgggcagtta atgttgcaca ggttattgat agcgaaaccg cagataatct ggaaaaaacc | 900 |
| accgcagcac tgagcattct gcctggtatt ggtagcgtta tgggtattgc agatggtgca | 960 |
| gtgcatcata taccgaaga aattgttgcc cagagcattg ccctgagcag tctgatggtt | 1020 |
| gcccaggcaa ttccgctggt tggtgaactg gttgatattg ttttgcagc ctataacttt | 1080 |
| gtcgagagca tcattaacct gtttcaggtt gtgcataaca gctataatcg tccggcatat | 1140 |
| agtccgggtc ataaaaccca gccgtttctg catgatggtt atgcagttag ctggaatacc | 1200 |
| gttgaagata gcattattcg taccggcttt caggtgaaa gcggtcatga tatcaaaatt | 1260 |
| accgcagaaa atacccgct gccgattgcc ggtgttctgc tgccgaccat tccgggtaaa | 1320 |
| ctggatgtga ataaatccaa aacccacatt agcgtgaacg tcgtaaaaat tcgtatgcgt | 1380 |
| tgtcgtgcaa ttgatggtga tgttacctttt tgtcgtccga aagtccggt ttatgttggt | 1440 |
| aatggtgttc atgcaaatct gcatgttgca tttcatcgta gctccagcga aaaaattcat | 1500 |
| agcaatgaaa ttagcagcga tagcattggt gttctgggtt atcagaaaac cgtggatcat | 1560 |
| accaaagtga atagcaaact gagcctgttc tttgaaatca aaagctaa | 1608 |

<210> SEQ ID NO 2
<211> LENGTH: 22
<212> TYPE: PRT
<213> ORGANISM: Artificial Sequence
<220> FEATURE:
<223> OTHER INFORMATION: PelB (pectate lyase B) Amino Acid Signal
      Sequence

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 3
<211> LENGTH: 33
<212> TYPE: DNA
<213> ORGANISM: Artificial Sequence
<220> FEATURE:
<223> OTHER INFORMATION: Kan-F

<400> SEQUENCE: 3
tgaaaaagga agagtatgag ccatattcaa cgg                          33

<210> SEQ ID NO 4
<211> LENGTH: 36
<212> TYPE: DNA
<213> ORGANISM: Artificial Sequence
<220> FEATURE:
<223> OTHER INFORMATION: Kan-R

<400> SEQUENCE: 4
aacttggtct gacagttaga aaaactcatc gagcat                       36

<210> SEQ ID NO 5
<211> LENGTH: 28
<212> TYPE: DNA
<213> ORGANISM: Artificial Sequence
<220> FEATURE:
<223> OTHER INFORMATION: pTAC-F

<400> SEQUENCE: 5
ctgtcagacc aagtttactc atatatac                                28

<210> SEQ ID NO 6
<211> LENGTH: 26
<212> TYPE: DNA
<213> ORGANISM: Artificial Sequence
<220> FEATURE:
<223> OTHER INFORMATION: pTAC-R

<400> SEQUENCE: 6
actcttcctt tttcaatatt attgaa                                  26

<210> SEQ ID NO 7
<211> LENGTH: 58
<212> TYPE: DNA
<213> ORGANISM: Artificial Sequence
<220> FEATURE:
<223> OTHER INFORMATION: phoA-pTAC-1-F

<400> SEQUENCE: 7
ctttgttttt atttttttaat gtatttgtac ataggagata taatatgaag cttcctcg    58

<210> SEQ ID NO 8
<211> LENGTH: 59
<212> TYPE: DNA
<213> ORGANISM: Artificial Sequence
<220> FEATURE:
<223> OTHER INFORMATION: phoA-pTAC-1-R

<400> SEQUENCE: 8
cgactataag tctcggccgt gacaacttta tgacagaatt tcagaaggat cctctacgc    59

<210> SEQ ID NO 9
<211> LENGTH: 52

```
<212> TYPE: DNA
<213> ORGANISM: Artificial Sequence
<220> FEATURE:
<223> OTHER INFORMATION: pelB-F

<400> SEQUENCE: 9
ctgctcctcg ctgcccagcc ggcgatggcc ggtgcagatg atgttgttga ta        52

<210> SEQ ID NO 10
<211> LENGTH: 51
<212> TYPE: DNA
<213> ORGANISM: Artificial Sequence
<220> FEATURE:
<223> OTHER INFORMATION: pelB-R

<400> SEQUENCE: 10
cagaccagca gcagcggtcg gcagcaggta tttaagctta tgcggccttg a        51

<210> SEQ ID NO 11
<211> LENGTH: 22
<212> TYPE: DNA
<213> ORGANISM: Artificial Sequence
<220> FEATURE:
<223> OTHER INFORMATION: phoA-SEQ-F

<400> SEQUENCE: 11
gcgtagagga tccttctgaa at                                         22

<210> SEQ ID NO 12
<211> LENGTH: 24
<212> TYPE: DNA
<213> ORGANISM: Artificial Sequence
<220> FEATURE:
<223> OTHER INFORMATION: pTAC-SEQ-R

<400> SEQUENCE: 12
ctgtatcagg ctgaaaatct tctc                                       24

<210> SEQ ID NO 13
<211> LENGTH: 21
<212> TYPE: DNA
<213> ORGANISM: Artificial Sequence
<220> FEATURE:
<223> OTHER INFORMATION: CRM197-433-F

<400> SEQUENCE: 13
gcagcagcgt tgaatatatc a                                          21

<210> SEQ ID NO 14
<211> LENGTH: 20
<212> TYPE: DNA
<213> ORGANISM: Artificial Sequence
<220> FEATURE:
<223> OTHER INFORMATION: EG-197(II)-F

<400> SEQUENCE: 14
gcgaactgaa aaccgttacc                                            20

<210> SEQ ID NO 15
<211> LENGTH: 20
<212> TYPE: DNA
<213> ORGANISM: Artificial Sequence
<220> FEATURE:
<223> OTHER INFORMATION: EG-197(II)-R

<400> SEQUENCE: 15
```

-continued

```
accaatacca ggcagaatgc                                                  20

<210> SEQ ID NO 16
<211> LENGTH: 39
<212> TYPE: DNA
<213> ORGANISM: Artificial Sequence
<220> FEATURE:
<223> OTHER INFORMATION: DXS-XhoI-F

<400> SEQUENCE: 16
actgctcgag taagttttga tattgccaaa tacccgacc                             39

<210> SEQ ID NO 17
<211> LENGTH: 30
<212> TYPE: DNA
<213> ORGANISM: Artificial Sequence
<220> FEATURE:
<223> OTHER INFORMATION: DXS-EcoRI-R

<400> SEQUENCE: 17
actggaattc ttatgccagc caggccttga                                       30
```